United States Patent [19]

VanRheenen

[11] 4,189,596
[45] Feb. 19, 1980

[54] PREPARING 2-ARYLALKANOIC ACID DERIVATIVES

[75] Inventor: Verlan H. VanRheenen, Portage, Mich.

[73] Assignee: The Upjohn Company, Kalamazoo, Mich.

[21] Appl. No.: 792,771

[22] Filed: May 2, 1977

Related U.S. Application Data

[63] Continuation-in-part of Ser. No. 777,598, Mar. 15, 1977, abandoned, which is a continuation-in-part of Ser. No. 689,366, May 24, 1976, abandoned.

[51] Int. Cl.$^2$ .................. C07C 63/52; C07C 69/76
[52] U.S. Cl. ........................ 560/105; 260/343.3 R; 560/51; 560/53; 560/126; 560/176; 562/462; 562/463; 562/496; 562/508; 562/578
[58] Field of Search ............... 260/515 R; 560/105; 562/496

[56] References Cited

U.S. PATENT DOCUMENTS

| | | | |
|---|---|---|---|
| 3,256,300 | 6/1966 | Wygant et al. | 260/343.3 R |
| 3,758,513 | 9/1973 | Heelsa | 260/343.3 R |
| 3,850,952 | 11/1974 | Kuo et al. | 260/343.3 R |
| 4,008,270 | 2/1977 | White | 260/515 R |
| 4,096,177 | 6/1978 | Baiocchi | 562/496 |

FOREIGN PATENT DOCUMENTS 820267 1/1975 Belgium .
2554895 7/1976 Fed. Rep. of Germany .
1265800 3/1972 United Kingdom .

OTHER PUBLICATIONS

Palazzo et al., Tetrahedron Letters, No. 46, pp. 4739–4742 (1968).

Primary Examiner—Jane S. Myers
Attorney, Agent, or Firm—John T. Reynolds

[57] ABSTRACT

2-Aryl-$C_2$ to $C_5$-alkanoic acids and esters thereof are prepared by heating a 2-(2-oxo-3-cyclohexenyl)-alkanoic acid or ester derivative in the presence of a sulfonic acid or a phosphonic acid at 75° C. to 130° C. while providing a means for removing water from the reaction mixture. In the process new butenolide derivative intermediates have been discovered. Alternatively, the 2-aryl-$C_2$ to $C_6$-alkanoic acids can be prepared from the butenolides by forming a mixture of the 2-(2-oxo-3-cyclohexenyl)-alkanoic acid with acetic anhydride in the presence of an acid scavenging base, allowing the mixture to stand for a time sufficient to form an acetate intermediate, heating the resulting mixture to about 75° C. to about 130° C. to form the betenolide intermediates. Thereafter these intermediates can be heated with sulfonic or phosphonic acid as above while removing water to form the 2-aryl-$C_2$ to $C_6$-alkanoic acid or adding a carboxylic acyl halide and water to form acetic acid and mineral acid in the mixture, and this resulting mixture can be heated to 75° C. to 130° C. for a time sufficient to form 2-aryl-$C_2$ to $C_6$-alkanoic acid products which have a variety of uses.

14 Claims, No Drawings

PREPARING 2-ARYLALKANOIC ACID DERIVATIVES

CROSS-REFERENCES

This is a continuation-in-part of application Ser. No. 777,598, filed Mar. 15, 1977, now abandoned, which is a continuation-in-part of application Ser. No. 689,366, filed May 24, 1976, now abandoned.

INTRODUCTION

This invention relates to chemical processes for preparing 2-arylalkanoic acid compounds. More particularly, this invention provides an improved process for preparing 2-aryl-$C_2$ to $C_6$-alkanoic acids. In its preferred aspects this invention is particularly concerned with providing an improved process for preparing 2-aryl-$C_2$ to $C_6$-alkanoic acids which are useful as anti-inflammatory, analgesic and anti-pyretic drug compounds, e.g., 2-(4-isobutyl)-phenyl)propionic acid, now known generally as ibuprofen.

BACKGROUND OF THE INVENTION

2-Arylalkanoic Acids

A variety of arylalkanoic acids are now known to be useful as active anti-inflammatory, analgesic, anti-pyretic, anti-thrombotic pharmaceutical drug products. A few of the better known of these drug compounds include the 2-arylpropionic acid derivatives such as fenoprofen which is 2-(3-phenoxyphenyl)propionic acid and related compounds which are described in Marshall U.S. Pat. No. 3,600,437, ibuprofen which is 2-(4-isobutylphenyl)propionic acid and which is described with other related compounds in Nicholson et al U.S. Pat. No. 3,385,886, naproxen which is 2-(6-methoxy-2-naphthyl)propionic acid which is described with other related compounds in Belgian Pat. No. 747,812 (Derwent Index No. 71729R-B). In addition, a variety of other 2-aryl-$C_2$ to $C_6$-alkanoic acid compounds are described in the medical, pharmaceutical, agricultural and patent literature, including the above patent references as well as Shen U.S. Pat. No. 3,624,142 and Adams et al U.S. Pat. No. 3,793,457 which patents describe some fluoro-substituted biphenylalkanoic acids.

Thus, a large variety of 2-aryl-$C_2$ to $C_6$-alkanoic acids having a variety of practical uses are known and more of such compounds will undoubtedly be discovered and described in the future patent and other technical literature.

Prior Processes

The above patent references also describe a variety of process routes for preparing useful 2-aryl-$C_2$ to $C_6$-alkanoic acids. However, some of the prior processes suffer a variety of disadvantages including expensive starting materials, dangerous by-products, undesired and gross quantities of by-products necessitating substantial expense in destroying or getting rid of such by-products. As a result chemists skilled in chemical process research continue to study and search for improved processes for making the more economically significant 2-aryl-$C_2$ to $C_6$-alkanoic acids, and particularly the 2-arylpropionic acids.

Most of such processes have involved the use of aromatic ring moiety reactants. For example, processes have been described for preparing the 2-(substituted phenyl)propionic acids (a) from aromatic glycidonitriles (see Argentine Pat. Nos. 198,097 and 198,595), (b) from aromatic glycidyl esters (see German Offenlegungsschrift No. 2,404,159, published Aug. 29, 1974), (c) from aromatic alkyl cyanides and by a variety of other process routes, all of which involve the use of an aromatic moiety. See, for example, U.S. Pat. No. 3,600,437 for a description of a number of those processes.

More recently Belgian Pat. No. 820,267 described a process for preparing p-isobutyl-hydratropic acid, also now named 2-(4-isobutylphenyl)propionic acid (ibuprofen) by treating an aliphatic compound of the formula

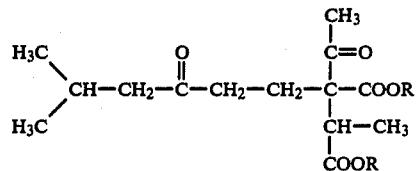

where each R is a $C_1$ to $C_5$-alkyl, with a strong acid aqueous solution at 200° C. to 240° C., or in a dry state with a strong acid salt and an organic base for from 30 minutes to 3 hours. That Belgian patent also indicates that its formula (II) compound need not be isolated before acid treatment but can be obtained in the crude product form by reacting the vinyl-isobutyl-ketone with alkyl α-acetyl-α-methylsuccinate, or by reaction of an acetoacetic acid ester with an alkyl α-halopropionate and then with the vinyl-isobutyl-ketone.

That Belgian patent also refers to prior processes and to some prior patents, including British Pat. No. 1,265,800 which discloses the synthesis of methyl or ethyl 2-(4-isobutyl-2-oxocyclohex-3-enyl)propionate in some undisclosed yield. The Belgian Pat. No. 820,267 indicates that when they repeat the pertinent experiments of the British Pat. No. 1,265,800 they obtained yields of less than 5 percent; and concluded the process for preparing p-isobutyl-hydratropic acid (ibuprofen) as described in British Pat. No. 1,265,800 had no industrial application. The Belgian Patent points out that the advantages of its described process for preparing 2-(4-isobutyl-2-oxo-3-cyclohexenyl)propionic acid intermediate is that it does not require the use of expensive and dangerous reagents such as silver nitrate or cyanide ion. That Belgian patent process for the production of ibuprofen from 2-(4-isobutyl-2-oxo-3-cyclohexenyl)propionic acid is based upon the aromatization which occurs when a dialkyl-α-acetyl-α-[(5-methyl-3-oxo)-hexyl]-α'-methylsuccinate is heated to temperatures of about 200° C. to 240° C. with strong acid, but the Belgian patent process requires temperature over 200° C.

The British Pat. No. 1,265,800 process requires the use of corrosive materials and also requires the use of heating temperatures over 200° C. Persons skilled in this process art are searching for improved processes for making these valuable drug compounds while avoiding the use of polymerizable intermediates, corrosive materials, and the high temperatures described in those references.

OBJECTS OF THE INVENTION

It is an object of this invention to provide an operationally simple, high yielding, one-step process for the manufacture of 2-aryl-$C_2$ to $C_6$-alkanoic acids.

It is a further object of this invention to provide new butenolide derivative compounds which are useful as intermediates in processes for preparing useful 2-aryl-$C_2$ to $C_6$-alkanoic acid compounds.

It is another object of this invention to provide an alternative method for preparing useful 2-aryl-$C_2$ to $C_6$-alkanoic acids via butenolide intermediates.

Other objects, aspects and advantages of this invention will become apparent from reading the remaining specification and claims.

SUMMARY OF THE INVENTION

This invention provides a process for preparing 2-aryl-$C_2$ to $C_6$-alkanoic acids and esters (I) by heating at about 75° C. to 130° C. a mixture containing at least one compound from the group consisting of (A) a 2-(substituted-2-oxo-3-cyclohexenyl)-$C_2$ to $C_6$-alkanoic acid or ester (II), a succinate acid or ester precursor thereof (III), an α-acetyl-α-(substituted-3-oxopropyl)succinic acid or ester derivative (IV), or a butenolide compound (V) and (VI), in the presence of a sulfonic or phosphonic acid while providing a means for removing water from the mixture during the heating operation until the 2-aryl-$C_2$ to $C_6$-alkanoic acid, ester or mixture thereof is formed.

This invention also provides new butenolide compounds (V) and (VI) per se. These compounds can be and are prepared in the reaciton mixture of the above process of this invention.

Another aspect of this invention provides a process for preparing 2-aryl-$C_2$ to $C_6$alkanoic acids (I) through these butenolides by forming a mixture containing the 2-(substituted-2-oxo-3-cyclohexenyl)-$C_2$ to $C_6$-alkanoic acid (II), acetic anhydride and an acid scavenging base; allowing the mixture to stand until an acetate intermediate (XI) is formed, heating the resulting mixture to from about 75° C. to about 130° C. for a time sufficient to form a mixture containing at least one of the butenolide intermediates (V) and (VI), adding a carboxylic acyl halide, e.g., acetyl chloride, and a stoichiometric amount of water to form acetic acid and mineral acid, e.g., hydrochloric acid, in the mixture and then heating the mixture at about 75° C. to about 130° C. for a time sufficient to form the 2-aryl-$C_2$ to $C_6$-alkanoic acid or ester product (I). Alternatively, the buteneloide intermediate (V) and (VI) can be mixed with a sulfonic or phosphonic acid and heated to form about 75° C. to about 130° C. while providing a means for removing water from the mixture for a time sufficient to form a 2-(aryl)-$C_2$ to $C_6$-alkanoic acid or ester product (I) of the process.

DETAILED DESCRIPTION OF THE INVENTION

More specifically, this invention provides an improved process for preparing compounds of the formula

(I)

wherein R is hydrogen or $C_1$ to $C_4$-alkyl, $R_1$ is hydrogen, $C_1$ to $C_6$-alkyl or mixtures thereof, and Ar is an aromatic radical containing 6 to 12 carbon atoms in which the aryl ring portion thereof is preferably phenyl bonded to the alkanoic acid carbon atom adjacent to the carboxyl group at an aryl ring carbon atom, which, comprises heating at a temperature of from 75° C. to about 130° C. a mixture containing (A) at least one compound having a formula selected from the group consisting of (a) a compound of the formula

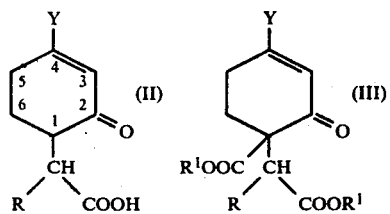

wherein R and $R^1$ are as defined above; and

Y, taken separately, preferably is $C_3$ to $C_5$-alkyl, or hydrogen;

(b)

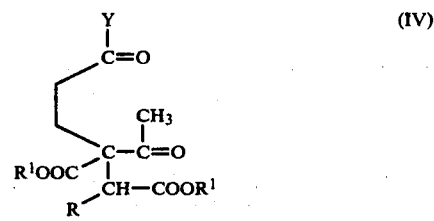

wherein R, $R^1$ and Y are as defined above:

(c)

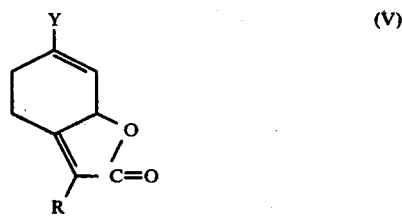

wherein R, Y and Z are as defined above, and (d) a compound of the formula

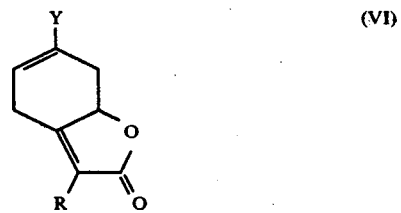

wherein R and Y are as defined above, and (B) a sulfonic acid or a phosphonic acid, preferably in each acid such an acid having from 1 to 12 carbon atoms, while providing a means for removing water from the reaction mixture during the heating operation for a time sufficient to form a formula I compound. The heating of the reaction mixture containing reactants (A) and (B) may be done neat, that is, without added liquid diluent or solvent. However, it has been found that the reaction proceeds more efficiently to produce higher yields if the reaction is diluted with a non-polar organic liquid, preferably one which forms an azeotrope with which in the heated mixture. fWe have found that the product (1) from starting material II, III, or IV in its ester form in the above heating step is usually a mixture of its 2-aryl-$C_2$ to $C_6$-alkanoic acid, and its corresponding ester, so we include such mixtures in the definition of the $R^1$ moiety. However, this acid/ester mixture is thereafter treated with a hydrolyzing base to remove the ester groups and to form the salt form of the product I. The free acid form of product (I) can be regenerated from the salt by known methods.

Any readily available sulfonic or phosphonic acid can be used in the process. However, as a practical economic matter such acids having from 1 to 12 carbon atoms in the organic group of such acids are of primary interest. Sulfonic and phosphonic acids which have solubility in the non-polar organic liquid diluent for the reactants are preferred. The $C_1$ to $C_{12}$-alkanesulfonic, $C_1$ to $C_{12}$-alkanephosphonic, $C_6$ to $C_{12}$-aryl and the $C_7$ to $C_{12}$-alkarylsulfonic and -phosphonic acids such as methanesulfonic, ethanesulfonic, dodecanesulfonic, phenylsulfonic, or preferably p-toluenesulfonic acid, or methylphosphonic, ethanephosphonic dodecylphosphonic, phenylphosphonic, p-tolylphosphonic acid, or the like are examples of such acids. These acids may be used in their hydrated form. p-Toluenesulfonic acid monohydrate is our sulfonic acid of choice when ibuprofen is being prepared by this process in toluene. We have found that phenylphosphonic acid also works quite well and would be a preferred phosphonic acid. Other sulfur and phosphorus containing acids such as ortho-phosphoric acid and sulfuric acid have been tried but they do not work nearly as well as do sulfonic and phosphonic acids in the process of this invention.

A preferred embodiment of this invention is to use this process to prepare ibuprofen by heating to from about 100° C. to about 130° C. in a non-polar organic liquid solvent or diluent which azeotropes with water, preferably at reflux in a toluene containing diluent medium (about 110° C.), a mixture containing (A) at least one compound of the formulas:

(a)

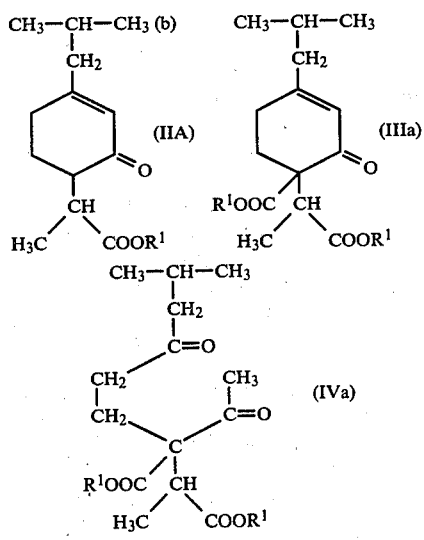

wherein each formula $R^1$ is hydrogen, a $C_1$ to $C_6$-alkyl or mixtures thereof in the particular batch used, and (B) a substantially equimolar amount, relative to the total current of starting materials IIa, IIIa and IVa, of p-toluenesulfonic acid or its hydrate or phenylphosphonic acid, for a time sufficient to form an ibuprofen compound of the formula

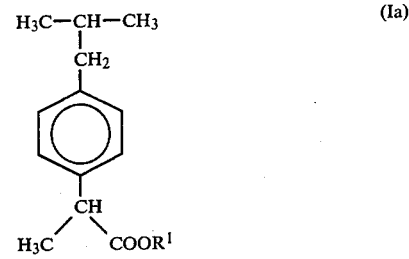

wherein $R^1$ is as defined above. Thereafter, the preferred process includes the step of adding water after the heating step in an amount sufficient to hydrate the p-toluenesulfonic acid so that the hydrated acid separates from the liquid phase of the mixture. The reaction mixture containing the crude ibuprofen product can then be treated with an alkali metal hydroxide, carbonate or bicarbonate preferably in aqueous solution form, to form ibuprofen alkali metal salt. Any alkali metal basic compound could be used in this step but as a practical, economic matter only sodium, potassium or lithium hydroxide bicarbonate or carbonate would be used.

As an added embodiment of this invention it has been found that addition of acetone or an equivalent ketone, but preferably acetone, to an aqueous alkali metal ibuprofen or other 2-aryl-$C_2$ to $C_6$ alkanoate salt solution is very effective to precipitate the alkali metal ibuprofen salt from the liquid phase and this property of acetone in these mixtures provides a simple, effective means for separating the ibuprofen or other 2-aryl-$C_2$ to $C_6$-alkanoic acid, as its salt, from its reaction mixture. The amount of acetone added can be any amount which will cause the salt to precipitate but can range from say equimolar amounts relative to the salt content of the mixture to volume excesses of acetone relative to the aqueous phases, depending on agitation conditions and the amount of time one allows for the salt to separate.

The crude alkali metal ibuprofen or other 2-aryl-$C_2$ to $C_6$ alkanoate salt can be then converted to its corresponding acid by acidification with an acid strong enough to convert the ibuprofen or other 2-aryl-$C_2$ to $C_6$-alkanoate salt to its free acid form followed by extraction, drying and evaporation procedures. For example, the ibuprofen or other 2-aryl-$C_2$ to $C_6$-alkanoate alkali metal salt in aqueous medium can be acidified with an economical mineral acid such as 6 N sulfuric or hydrochloric acid to form the acid and the reaction mixture can be extracted one or more times with non-polar, organic liquid solvent such as Skelly-solve ® B. The combined organic phases containing the acid can be separated from the aqueous phase and dried over a chemical drying agent such as sodium sulfate and then evaporated to leave as residue the crystalline ibuprofen or other acid product, which can be collected and readied for its ultimate use in pharmaceutical formulations or agricultural or other practical compositions as known in the art.

As indiated by the above listed starting materials this invention provides a low temperature, high yielding process for the manufacture of ibuprofen and related 2-aryl-$C_2$-$C_6$-alkanoic acids from α-acetylsuccinate ester derivatives of formula IV above. Such α-acetylsuccinate ester derivative starting materials can be prepared by Michael condensation reaction analogous to the procedures described in British Pat. No. 1,265,800, cited above. Thus, it is not necessary according to this invention to isolate and separatly start this process with the 2-(substituted-2-oxo-3-cyclohexenyl)$C_2$ to $C_6$-alkanoic acid or ester (II) per se. Such compounds (II) are formed in situ in the process of this invention when the starting reaction mixture contains the α-acetylsuccinate ester (IV).

During the heating step of the process of this invention, water production, ester hydrolysis, and decarboxylation are noted. Water can be continuously removed by attaching a Dean-Start trap or equivalent apparatus to the reaction vessel. Optionally, the reaction mixture may be switched from reflux to partial takeoff of distillate, or it can be distilled through molecular sieves, e.g., 4 A molecular sieves, which absorb both water and alcohol. Because of the efficient azeotrope formation of toluene/ethanol/water (about 57/37/12 v/v/v, respectively) it is preferred to use toluene as the non-polar diluent when ibuprofen is being prepared. This removal of alcohol and water shifts the equilibrium of any α-acetylsuccinate derivative (IV) containing reaction mixture toward the production of a 2-(substituted-2-oxo-3-cyclohexenyl)-propionic acid (II). Further reflux of the reaction mixture under water separating conditions, e.g., with a Dean-Stark trap attached to the reaction vessel, converts the 2-(substituted-2-oxo-3-cyclohexenyl)propionic acid to butenolides V and VI above, which aromatize at different reaction rates to the 2-aryl-$C_2$ to $C_6$-alkanoid acid or ester product (I).

It has also been found according to this invention that the process of this invention produces butenolide derivative compounds of formulas V and VI above. These butenolide compounds can be isolated if desired, but they need not be isolated since they are useful as chemical intermediates in the process of this invention to prepare the 2-aryl-$C_2$ to $C_6$-alkanoic acid and ester products (I). Preferred examples of such compounds are those of formulas (V) and (VI) wherein Y is isobutyl and R is methyl.

These preferred butenolide intermediates (V) and (VI) are useful as intermediates for preparing the known drug compound ibuprofen in the process of this invention.

If desired, the conditions of this process of this invention can be adjusted to produce larger quantities of these butenolide intermediate compounds (V) and (VI). For example, the 2-(substituted-2-oxo-3-cyclohexenyl)-alkanoic acid or esters (II) reaction mixture can be treated with only catalytic amounts, say 1 to 10 percent, of the sulfonic or phosphonic acid in a non-polar, azeotroping solvent to form a mixture containing mostly that of butenolide (VI) and a minor amount of butenolide (V). Treatment of the 2-(substituted-2-oxo-3-cyclohexenyl)alkanoic acid (II) with acetic anhydride in the presence of an acid scavenging base which does not destroy the reactants, e.g., with potassium carbonate or pyridine, at room temperature for a time sufficient to form the unstable intermediate XI of the formula:

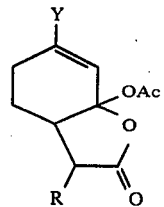
(XI)

wherein R and Y are as defined above, and -OAc denotes acetoxy, and then followed by heating of that mixture to 75° C. to 110° C. yields a mixture in which the butenolide intermediate content contains a major amount of structures V and minor amounts of butenolide structure VI.

Treatment of these butenolides with a mineral acid such as sulfuric acid or hydrochloric acid in acetic acid (or acetyl chloride and water) aromatizes butenolide to its 2-aryl-$C_2$ to $C_6$-alkanoic acid (I). Treatment of butenolide VI with p-toluenesulfonic acid according to this invention converts to its 2-aryl-$C_2$-alkanoic acid (I) product.

Although the detailed examples hereinbelow are drawn for the most part to describe the process for the preparation of the preferred product ibuprofen, the process of this invention can also be adapted to the production of other similar 2-aryl-$C_2$ to $C_6$-alkanoic acid products.

During the heating step water in the reaction mixture is removed by any conventional chemical, physical or mechanical means. To insure complete and efficient reaction it is preferred that the sulfonic or phosphonic acid be used in approximately molar equivalent amounts relative to the starting material (A) which is actually or theoretically in the reaction mixture, although such stoichiometric proportions of sulfonic or phosphonic acid are not required. It is just that the preferred sulfonic or phosphonic acid can be essentially quantitatively recovered for reuse in the process so that it is not necessary to economize on its use.

Any non-polar organic liquid diluent which is a stable liquid and preferably dissolves the reactants in the heating temperature range can be used in the process of this invention. Preferably this organic liquid also boils in this temperature range and forms an azeotrope with water and any alcohol which may be generated during the heating step. Toluene is our preferred solvent which ibuprofen is being prepared but other organic liquids such as xylene, mesitylene, heptane, octane, and commerical mixtures of such organic liquids having boiling points ranges within the ranges of the heating step of the process of this invention including Skellysolve ® C and D (See Merck Index, Eighth Edition, page 951) can be used. Mixtures of organic liquid which contain polar ingredients as well as one or more of the above non-polar ingredients and having boiling boint ranges within the heating range may also be used.

The means for removing or inactivating water in the reaction mixture during the heating operation can be provided by chemical or physical procedures known in the art, or by combinations of both chemical and physical means.

Preferably, however, we have obtained our best yields of 2-(aryl)$C_2$ to $C_6$-alkanoic acid or ester product (I) when the reaction mixture includes a liquid or mixture of liquids which form an azeotrope with water, which water containing azeotrope is distilled out of the reaction mixture during the heating operation. Numerous types of chemicals are known to form binary or tertiary water-containing azeotropes having boiling points sufficient for distllation during the heating operations. Such chemicals include $C_5$ to $C_8$ alkanes, and $C_6$ to $C_8$-aromatic hydrocarbons, halogenated hydrocarbons, particularly those containing from 1 to 6 carbon atoms and from 1 to 4 chlorine or bromine atoms, ethers, esters, organic acids, ketones, aldehydes, and the like, as set forth in various chemical handbooks, e.g., *Handbook of Chemistry*, edited by N. A. Lange, ninth edition (1956) published by Handbook Publishers Inc., Sandusky, Ohio, pp. 1484 to 1486 and 1493 and in Chemical Rubber Co., Handbook of Chemistry and Physics, 45th Edition, pp. D-1 to C-18 (1964–65). We prefer that the liquid that is used to form a water containing azeotrope in the reaction mixture be a readily available, economical, inert organic liquid which may or may not be a solvent for the reaction mixture. Examples of suitable water-azeotrope forming liquids that are heavier than water which may be used include 1,2-dichloroethane, chloroform, methylene chloride and carbon tetrachloride. Examples of suitable water-azeotrope forming liquids that are lighter than water which may be used include benzene, toluene, xylene, pentane, hexane, heptane, and the like.

We have found that the 2-(substituted-2-oxo-3-cyclohexenyl)$C_2$ to $C_6$-alkanoic acids (II) can be converted to the corresponding 2-(aryl)$C_2$ to $C_6$-alkanoic acids (I) by heating them neat in molten p-toluene-sulfonic acid monohydrate or an equivalent sulfonic or phosphonic acid at about 120° C. for 5 to 20 hours, but the yield of the desired 2-(aryl)$C_2$ to $C_6$-alkanoic acid is not as high as when a solvent for the reaction mixture is used.

The invention is exemplified in more detail by the following examples which are not intended to limit the scope of the invention but only to illustrate its operability under various conditions. All temperatures are in degrees centigrade unless otherwise indicated.

EXAMPLE 1

Process using toluene solvent.

In a 10 ml. flask there was placed about 1.01 gm. ($4.52 \times 10^{-3}$ mole) of crystalline 2-(4-isobutyl-2-oxo-3-cyclohexenyl)propionic acid, 0.8596 gm. of p-toluenesulfonic acid monohydrate ($4.52 \times 10^{-3}$ mole), and 5 ml. of toluene.

The flask was then fitted with a Dean-Stark trap and a condenser under a nitrogen atmosphere. The flask and its contents was then heated to reflux (b.p. toluene=110° C.) in an oil bath collecting water in the Dean-Stark trap.

After a total of about 1 hour and twenty minutes, a thin layer chromatographic (TLC) analysis of a sample of the reaction mixture indicated that almost all of the 2-(4-isobutyl-2-oxo-3-cyclohexenyl)propionic acid had been consumed. The reaction mixture was heated for another 4.5 hours at reflux to insure complete reaction. (Total of about 6 hours reaction time). The mixture was then allowed to cool to room temperature, and a TLC analysis of the reaction mixture showed that the reaction was complete.

To recover the ibuprofen product from the reaction mixture, the flask and its contents were treated as follows:

About 50 μl. of water was added to the reaction mixture flask precipitating p-toluenesulfonic acid monohydrate. The mixture was cooled in an ice bath and filtered. The filtered material was washed with toluene and the filtrate and the toluene washings were combined.

The ibuprofen was recovered from the toluene mixture by extracting the toluene phase with 0.2062 gm. of sodium hydroxide (1.805 gm.=$4.52 \times 10^{-3}$ mole) dissolved in about 20 ml. of water. The toluene phase was extracted a second time with a 5 percent sodium bicarbonate solution. The combined aqueous basic fractions were back extracted with Skellysolve ® B to remove any neutrals (organic soluble materials). The combined Skellysolve B and toluene fractions were combined, dried over sodium sulfate and evaporated to a gold residue weighing 89.3 mg. (96 percent).

The aqueous basic fraction containing sodium ibuprofen salt was acidified with 6N sulfuric acid, sodium chloride was added, and then extracted twice with Skellysolve B to take up the ibuprofen acid product therein. The Skellysolve B phase was dried over sodium sulfate and evaporated to leave as residue 867.7 mg. (93.2 percent yield) of ibuprofen which was 99.9 percent pure by gas liquid chromatographic (GLC) analysis.

A 0.7895 gm. portion of the ibuprofen product was re-dissolved in 3 ml. of hot Skellysolve B and after cooling the solution the ibuprofen re-crystallized to yield 0.6982 gm. of white crystalline ibuprofen, M.P. 74.5° C. to 75° C.

EXAMPLE 2

Process using molten p-toluenesulfonic acid.

A 0.9756 gm. portion of 2-(4-isobutyl-2-oxo-3-cyclohexenyl)propionic acid ($4.265 \times 10^{-3}$ mole) and 1.0046 gm. of p-toluensulfonic acid monohydrate (m. p. 104° C. to 106° C.) were added to a 15 ml. flask under nitrogen, the flask was fitted with a condenser and a magnetic stirring bar. The flask and its contents were heated in an oil bath for a total of about 14 hours, after which an additional 0.2009 gm. of p-toluenesulfonic acid was added, and heating was continued until a total heating time of 23 hours was completed.

The resulting reaction mixture was dissolved in toluene and crystals of p-toluenesulfonic acid precipitated and were filtered after addition of one mole equivalent of water. The toluene phase was extracted with 5 percent sodium bicarbonate solution, dried over sodium sulfate and evaporated to a brown oil weighing 0.0739 gm. (8.2 percent of theoretical ibuprofen yield).

The aqueous sodium bicarbonate phase was acidified and extracted three times with Skellysolve B which was dried over sodium sulfate, and evaporated to leave crude ibuprofen product weighing 0.7065 gm. (78.8 percent of theoretical ibuprofen yield). This yield was obtained despite spillage of the reaction mixture.

A 272.3 mg. portion of this crude ibuprofen was crystallized from Skellysolve B yielding 251.2 mg. of ibuprofen (92.3 percent yield).

EXAMPLE 3

Process using catalytic amounts of acid catalyst.

To a 15 ml. one-necked flask equipped with Dean-Stark trap and condenser, was added 0.0937 gm. of p-toluensulfonic acid monohydrate, 0.9935 gm. of crystalline 2-(4-isobutyl-2-oxo-3-cyclohexenyl)propionic acid, and 4 ml. toluene. The mixture was heated to reflux under nitrogen. After 5 hours of heating, TLC and GLC analysis of the reaction mixture showed minor amounts of ibuprofen product and 2-(4-isobutyl-2-oxo-3-cyclohexyl)propionic acid, and a major amount of two butenolide intermediates VA and VIA, which have been identified as being:

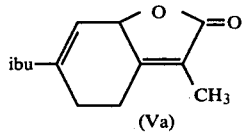 and 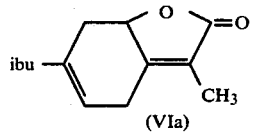

(Va)     (VIa)

where ibu denotes an isobutyl group.

Isolation of Va and VIa can be accomplished by extracting this cooled reaction mixture with 5 percent aqueous sodium bicarbonate, washing the toluene phase with water, drying it over sodium sulfate and evaporation of the toluene. The residual oil containing mostly (VIa) and a minor amount of (Va) is chromatographed over silica gel giving as oils pure Va and VIa having the following physical properties:

Va:

60 MHz (CDCl$_3$) 0.87 sextet (6H); 1.83 doublet (5H) resolves into a 2H singlet and 3H triplet on addition of Eu(FOD)$_3$; 5.22 singlet 1H, 5.64 ppm singlet (1H). 1R (CHCl$_3$) 1750, 1700 cm$^{-1}$.

$\lambda_{max}^{MeOH}$ 213 (7,500); 278 m$\mu$ sh ($\epsilon$ 674)

mass spectrum: 206 (m+), 177, 149.

VIa:

60 MHz NMR (CDCl$_3$) 0.90 (6H), 1.80 (5H), 4.96 quartet (1H) 5.45 quartet (1H)

IR 1750, 1695 cm.$^{-1}$ $\lambda_{max}^{MeOH}$ 220 m$\mu$ ($\epsilon$ 5850)

mass spectrum: 206 (m+), 177, 163, 149.

Subjecting each of the intermediates, Va and VIa to p-toluene sulfonic acid in refluxing toluene as before, produces ibuprofen.

EXAMPLE 4

Preparing ibuprofen from diethyl α-acetyl-α-(5-methyl-3-oxo-hexyl)-β-methylsuccinate containing mixture.

To a 110 ml., round-bottomed flask fitted with condenser and Dean-Stark trop there was added 4.339 gm. of a mixture containing:

(A) diethyl α-acetyl-α-(5-methyl-3-oxo-hexyl)-β-methylsuccinate. (IVa), a compound of the formula:

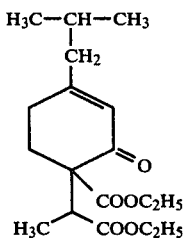

a compound of the formula:

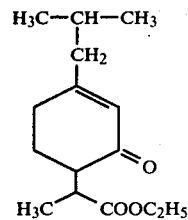

and (B) 2.443 gm. of p-toluenesulfonic acid monohydrate and 17 ml. of toluene.

Under an inert atmosphere of nitrogen, the flask and its contents were refluxed for 6.5 hours with water removal. Water (115 μl.) was then added to reaction mixture, momentarily cooled, and reflux was continued for another 16 hours. TLC analysis showed the reaction to be complete to a mixture of ibuprofen and its ethyl ester.

To the cooled reaction mixture was added 0.23 ml. of water, and the resulting precipitate of p-toluene-sulfonic acid monohydrate was filtered, washed with toluene, and dried.

The toluene filtrate under nitrogen was treated with 4.8 ml. of 33 percent aqueous sodium hydroxide at 60° C. for 22 hours. The upper organic layer was separated from the cooled reaction mixture by decantation, 5 ml. of acetone was added to the remaining basic aqueous layer and the resulting slurry of ibuprofen sodium salt was cooled at 0° C. for 2 hours, filtered and washed with cold acetone.

This ibuprofen sodium salt in 5 ml. of water was acidified with 6N H$_2$SO$_4$, and extracted twice with Skellysolve B. The combined organic phases were dried over sodium sulfate and evaporated to give 2.03 gm. of crystalline ibuprofen. The yield was 79 percent.

EXAMPLE 5

Process using a phosphonic acid.

A mixture containing 1.00 gm. (4.46 mmole) of 2-(4-isobutyl-2-oxo-3-cyclohexenyl)propionic acid and 0.70 gm. (4.46 mmole) of phenylphosphonic acid in 5 ml. of toluene is refluxed at about 110° for about 20 hours. The water formed is removed during the course of the reaction with an appropriate trap.

The phenylphosphonic acid is recovered by filtering it out of the reaction mixture. The ibuprofen [2-(4-isobutylphenyl)propionic acid] is then separated from neutral biproducts by extracting the filtered reaction mixture with 20 ml. of 10 percent sodium hydroxide in water solution. The basic phase containing dissolved sodium 2-(4-isobutylphenyl)propionate is then re-acidified with 6N sulfuric acid and the ibuprofen content is extracted from the acidified mixture with Skellysolve B from which solution ibuprofen crystallizes on cooling.

EXAMPLE 6

Process using molten p-toluenesulfonic acid with acetic anhydride as water scavenger.

To a melt of 1.216 g. of p-toluenesulfonic acid monohydrate (6.31 mmole) and 0.60 ml. of acetic anhydride (6.31 mmole) at 94° C. was added 1.01 g. of 2-(4-isobutyl-2-oxo-3-cyclohexenyl)propionic acid. This mixture was heated under nitrogen for 35 hours at 115° C. A 5 ml. quantity of heptane was added to the hot reaction mixture and decanted. This operation was carried out four times. The decantate was concentrated, extracted with 5 percent sodium bicarbonate aqueous solution, and the aqueous phase obtained was acidified to pH 2 and extracted with Skellysolve B. Drying over sodium sulfate and evaporation of this Skellysolve B phase yielded 0.855 g. (92.3 percent yield) of crystalline ibuprofen assaying 97.5 percent pure by gas liquid chromatography (GLC).

EXAMPLE 7

Preparation of ibuprofen from Michael adduct mixture.

A crude mixture (about 400 g.) of compound IIa, above, where $R_1$ is ethyl (ethyl 2-(4-isobutyl-2-oxocyclohex-3-enyl propionate), compound IIIa, above, where $R_1$ is ethyl (diethyl α-methylα'-(4-isobutyl-2-oxocycylohex-3-enyl) succinate, and compound IVa above, where $R_1$ is ethyl (diethyl α-methyl-α'-acetyl-α'-(5-methyl-3-oxohexyl)succinate, (containing approximately 0.6 mole of ibuprofen-making starting materials and 403 g. (2.12 mole) of p-toluenesulfonic acid monohydrate) are stirred under nitrogen at 80° C. for two hours. Water is added to the reaction mixture in three portions (3×86 ml.) and an equivalent volume of each portion of water is distilled from the reaction mixture at about 120° C. (before the next portion of water was added). The time required for these distillations is about 4 hours. Toluene (695 ml.) is added and the mixture is distilled (at reflux) over 6.5 hours to aromatize the ene-one acids (IIa, IIIa and IVa) to form ibuprofen acid, 2-(4-isobutylphenyl)propionic acid, and to azeotrope away the water with a Dean-Stark trap.

The resulting solution is cooled to 35° C. and water is added to precipitate p-toluenesulfonic acid monohydrate. The resulting slurry is cooled to 0° C. to 5° C., stirred over 1 hour and filtered and washed with about 50 ml. of toluene. The p-toluenesulfonic acid monohydrate precipitate solid (filtered material) is suitable for recycling and reuse. About 80 percent, 323 g., of the p-toluene sulfonic acid monohydrate was recovered.

The toluene filtrate and wash are mixed with 10 percent aqueous sodium hydroxide (412.5 g.) and the resulting organic phase is re-extracted with 135 ml. of water, and the phases separated again. The combined aqueous phases are diluted with 200 g. of 50 percent sodium hydroxide solution after which 99.75 of solid hydroxide and 428 ml. of acetone are added. Upon cooling this aqueous base treated mixture to 0° C. to 5° C. and stirring for about 1.5 hours, sodium 2-(4-isobutylphenyl)propionate (sodium ibuprofen) crystallizes out. This crystalline precipitate is collected by filtration and washed twice with 0° C. acetone portions (2×175 ml.) to purify the sodium ibuprofen salt cake. The sodium ibuprofen salt cake is added to 352 ml. of water and Skellysolve B (mixed hexanes) or hexane, 630 ml., is added. Concentrated sulfuric acid (80 ml.) is added to bring the pH of the mixture to about 0.6 and the resulting mixture is warmed to about 42° C. to dissolve the ibuprofen acid in the mixture. The aqueous and organic phase are allowed to separate. The aqueous phase is discarded and the organic phase is washed with water, e.g., two 1200 ml. portions of water. The organic phase containing the dissolved ibuprofen acid is separated from the water phase and cooled to 0° C. to 5° C. and stirred for about 0.5 hours until crystallization of the ibuprofen acid is completed. The ibuprofen crystals are filtered and washed with hexane and dried to give 90 to 100 g. of ibuprofen acid.

I claim:

1. Process for preparing a compound of the formula

wherein R is hydrogen or $C_1$ to $C_4$-alkyl; $R^1$ is hydrogen, $C_1$ to $C_6$-alkyl or mixtures thereof; and Ar is

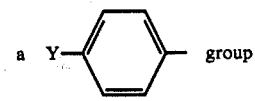

which is bonded to the alkanoic acid carbon atom adjacent to the carboxyl group at an aryl ring carbon atom, which comprises heating at a temperature of from about 75° C. to about 130° C. a mixture containing (A) at least one compound having a formula selected from the group consisting of

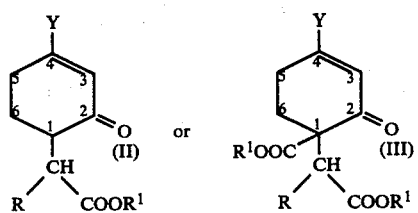

wherein R and $R^1$ are as defined above;
Y is $C_3$ to $C_5$-alkyl or hydrogen;

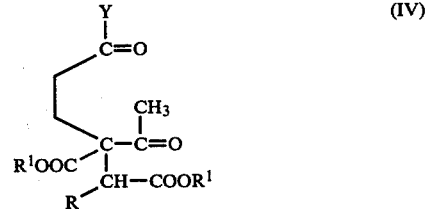

wherein R, $R^1$ and Y are as defined above;
a compound of the formula

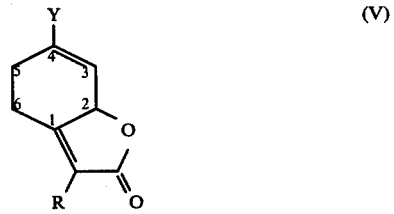

wherein R and Y are as defined above; and
a compound of the formula

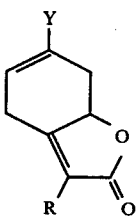 (VI)

wherein R and Y are as defined above; and (B) a $C_1$ to $C_{12}$-sulfonic acid or a $C_1$ to $C_{12}$-hydrocarbon phosphonic acid in a non-polar organic liquid which azeotropes with water for removing water from the reaction mixture during the heating operation, for a time sufficient to form a compound of formula I.

2. Process according to claim 1 wherein R is $C_1$ to $C_4$-alkyl, and Ar is a $C_3$ to $C_5$-alkylphenyl.

3. Process according to claim 1 which further includes the steps of subjecting the reaction mixture containing the 2-aryl-$C_2$ to $C_6$-alkanoic acid or ester product (I) to an aqueous alkali metal hydroxide treatment to form the 2-aryl-$C_2$ to $C_6$-alkanoate alkali metal salt and adding acetone to the alkali metal 2-aryl-$C_2$ to $C_6$-alkanoate salt phase to precipitate the alkali metal salt from the liquid phase.

4. Process according to claim 1 wherein a reaction mixture containing a compound of the formula

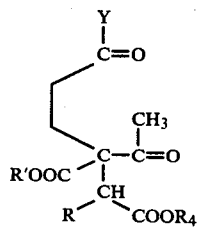 (IV)

where Y is $C_3$ to $C_5$-alkyl,
R is $C_1$ to $C_4$-alkyl,
$R^1$ is a hydrogen or a $C_1$ to $C_6$-alkyl; and a $C_1$ to $C_{12}$-sulfonic acid, in a non-polar organic liquid diluent which forms an azeotrope with water in the heated mixture, is heated at a temperature of from about 100° C. to about 130° C. for a time sufficient to form a compound of the formula

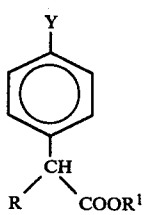 (IA)

wherein R, $R^1$ and Y are as defined hereinabove.

5. Process for preparing 2-(4-isobutylphenyl)propionic acid, its $C_1$ to $C_6$-alkyl ester or mixtures thereof which comprises heating at from about 100° C. to about 130° C. a mixture containing at least one compound of the formulas

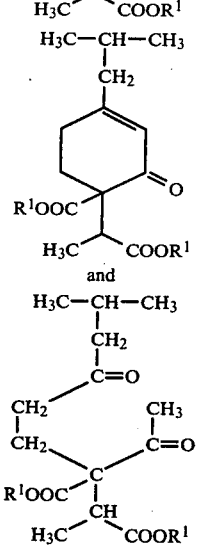

(IIa)

(IIIa)

and (IVa)

where in each formula $R^1$ is hydrogen or $C_1$ to $C_6$-alkyl, and a $C_1$ to $C_{12}$-sulfonic acid or $C_1$ to $C_{12}$ phosphonic acid in a non-polar organic liquid solvent which azeotropes with water at the boiling point of the solvent in the reaction mixture for a time sufficient to form an ibuprofen compound of the formula

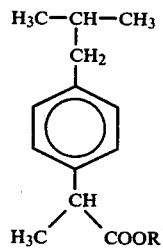 (Ia)

wherein $R^1$ is as defined above.

6. Process according to claim 5 which further includes the step of adding water after the heating step in an amount sufficient to hydrate the sulfonic acid in the mixture so that the hydrated sulfonic acid separates from the liquid phase of the mixture.

7. Process according to claim 6 which further includes the step of subjecting the reaction mixture containing the ibuprofen product compound to an aqueous alkali metal hydroxide carbonate or bicarbonate treatment to form ibuprofen alkali metal salt.

8. Process according to claim 7 which further includes the step of adding acetone to an aqueous alkali metal ibuprofen salt solution phase in an amount to precipitate the alkali metal ibuprofen salt from the liquid phase.

9. Process according to claim 8 which further includes the step of acidifying an ibuprofen alkali metal salt with an acid strong enough to convert the ibuprofen alkali metal salt to the acid ibuprofen.

10. Process according to claim 5 wherein reaction mixture is heated at reflux in toluene for a time sufficient to form the ibuprofen compound.

11. Process according to claim 5 wherein the sulfonic acid is p-toluenesulfonic acid.

12. Process which comprises (a) forming a mixture containing a compound of the formula

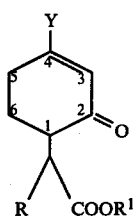
(II)

where Y is $C_3$ to $C_5$-alkyl or hydrogen;
R is hydrogen or $C_1$ to $C_4$-alkyl; and
$R^1$ is hydrogen, $C_1$ to $C_6$-alkyl or mixtures thereof; and
acetic anhydride, in the presence of an acid scavening base which does not destroy the reactants (b) allowing the mixture to stand for a time sufficient to form an acetate intermediate of the formula

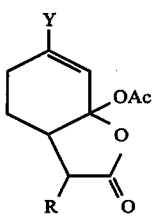
(XI)

which Ac denotes an acetyl group and R, Y and Z are as defined above, (c) heating the mixture from step (b) at a temperature of from about 75° C. to about 130° C. for a time sufficient to form a mixture containing at least one compound of the formula

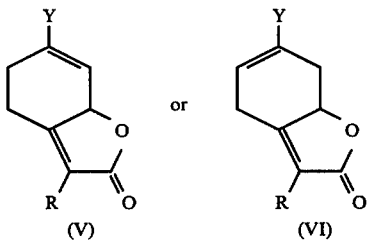
(V)     (VI)

(d) adding acetyl chloride and about one stoichiometrically equivalent of water, relative to the original acetic anhydride content of the mixture to form acetic acid and hydrogen chloride acid in the mixture, and then (e) heating the mixture from step (d) to form about 75° C. to 130° C. for a time sufficient to form a compound of the formula

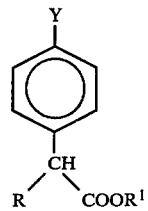
(I)

where R, $R^1$ and Y are as defined above.

13. Process which comprises (a) forming a mixture containing a compound of the formula

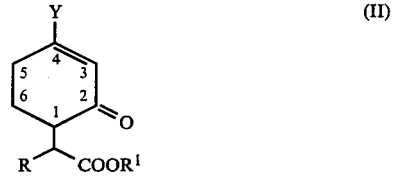
(II)

where Y is $C_3$ to $C_5$-alkyl or hydrogen;
R is hydrogen or $C_1$ to $C_4$-alkyl; and
$R^1$ is hydrogen, $C_1$ to $C_6$-alkyl or mixtures thereof;
Y is $C_3$ to $C_5$-alkyl or hydrogen; and
acetic anhydride, in the presence of an acid scavening base which does not destroy the reactants, (b) allowing the mixture to stand for a time sufficient to form an acetate intermediate of the formula

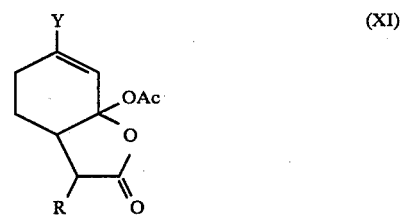
(XI)

which Ac denotes an acetyl group and R and Y are as defined above, (c) heating the mixture from step (b) at a temperature of from about 75° C. to about 130° C. for a time sufficient to form a mixture containing at least one compound of the formulae

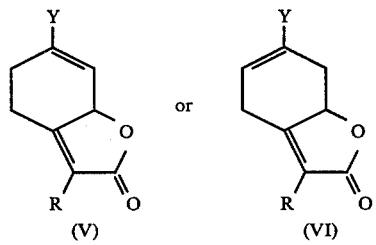
(V)     (VI)

(d) mixing the mixture from step (c) with a $C_2$ to $C_{12}$-sulfonic acid or a $C_1$ to $C_{12}$-phosphonic acid and heating the resulting mixture to from 75° C. to 130° C. in a non-polar organic liquid which azeotropes with water for removing water from the mixture for a time sufficient to form a compound of the formula

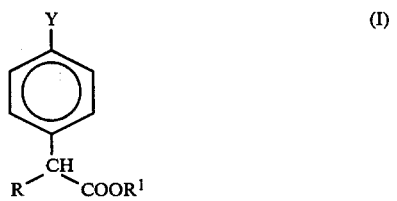
(I)

wherein R, $R^1$ and Y are as defined above.

14. Process according to claim 13 wherein Y is a $C_3$ to $C_5$-alkyl, R is $C_1$ to $C_4$-alkyl and $R^1$ is hydrogen, $C_1$ to $C_6$-alkyl or mixtures thereof.